United States Patent [19]

Sunkara et al.

[11] Patent Number: 4,499,072

[45] Date of Patent: Feb. 12, 1985

[54] PROCESS FOR TREATING DISEASES WITH ODC INHIBITORS

[75] Inventors: Sai P. Sunkara; Nellikunja J. Prakash, both of Cincinnati, Ohio

[73] Assignee: Merrell Dow Pharmaceuticals Inc., Cincinnati, Ohio

[21] Appl. No.: 460,224

[22] Filed: Jan. 24, 1983

Related U.S. Application Data

[63] Continuation-in-part of Ser. No. 445,349, Nov. 29, 1982, abandoned.

[51] Int. Cl.$^3$ .................... A61K 45/02; A61K 31/85; A61K 31/15
[52] U.S. Cl. .................................................... 424/85
[58] Field of Search ................ 424/85, 315, 325–326, 424/327

[56] References Cited

PUBLICATIONS

Chemical Abstracts, vol. 87, p. 27, Abstract No. 177545d, 1977.
Chemical Abstracts, vol. 97, p. 26, Abstract No. 192818v, 1982.
Chemical Abstracts, vol. 97, p. 203, Abstract No. 194368x, 1982.
Chemical Abstracts, vol. 93, p. 537, Abstract No. 47975a.
Sikora, K., British Medical Journal, vol. 281, pp. 855–858, 1980.

Primary Examiner—Blondel Hazel
Attorney, Agent, or Firm—Raymond A. McDonald; Stephen L. Nesbitt; Gary D. Street

[57] ABSTRACT

This invention relates to the improvement of the polyamine depletion effects of ornithine decarboxylase inhibitors and/or S-adenosylmethionine decarboxylase inhibitors, the improvement being effected by the use of interferon in conjunctive therapy with said inhibitors.

15 Claims, No Drawings

PROCESS FOR TREATING DISEASES WITH ODC INHIBITORS

This application is a continuation-in-part application of co-pending application Ser. No. 445,349, filed on Nov. 29, 1982 now abandoned.

This invention relates to the use of Interferon to enhance the treatment of rapidly-proliferating cell-growth disease states when these disease states are treated with irreversible inhibitors of ornithine decarboxylase.

That rapidly-proliferating cell-growth disease states are widespread throughout the world and affects a significant proportion of the population and that such diseases have been the subject of intensive research efforts is well known. Unfortunately, despite such efforts and despite some successes the overall control of these diseases has not been too satisfactory. Recently however, the pursuit in the alleviation and treatment of such disease states has shown promise by the discovery of irreversible inhibitors of enzymes which relate to the biosynthesis of the polyamines necessary for cell growth. Particularly useful enzyme inhibitors are those which produce in vivo irreversible inhibition of ornithine decarboxylase (ODC), the enzyme which catalyzes the decarboxylation of ornithine to putrescine.

The decarboxylation of ornithine to putrescine is the first step in the biosynthesis of the polyamines known as spermidine and spermine. Spermidine is formed by the transfer of an activated aminopropyl moiety from S-adenosyl S-methyl homocysteamine to putrescine, while spermine is formed by the transfer of a second aminopropyl group to spermidine. S-adenosyl S-methyl homocysteamine is formed by the decarboxylation of S-adenosylmethionine (SAM), a reaction catalyzed by the enzyme S-adenosylmethionine decarboxylase (SAM-DC). Since putrescine is a precursor of the polyamines, it is seen that blockade of the conversion of ornithine to putrescine, such as by inhibition of ODC, can provide a method for regulating the cellular levels of the polyamines.

The polyamines, which are found in animal tissues and microorganisms, are known to play an important role in cell growth and proliferation. The induction of cell growth and proliferation is associated with a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in the testes, ventral prostate, and thymus; in psoriatic skin lesions; and in other cells undergoing rapid growth processes.

It is also well known that the rapid proliferation of tumor tissue is marked by an abnormal elevation of polyamine levels. Hence, the polyamines may play an important role in the maintenance of tumor growth. It is thus believed that the ODC inhibitors may exert their therapeutic effect by blocking the formation of the polyamines and thereby slowing, interrupting, or arresting the proliferation and metastases of the tumor tissue.

In addition to the rather recent discovery concerning the use of irreversible inhibitors of ornithine decarboxylase, particularly with such compounds as α-difluoromethyl ornithine, the methyl and ethyl esters of monofluoromethyl dehydroornithine, the R,R-isomer of methyl acetylenic putrescine, and the like, combinations of these ODC inhibitors with chemical cytotoxic agents has also shown promise in the treatment of diseases characterized by the rapid proliferation of tumor tissue. Indeed, in the treatment of a malignant neoplastic disease it has been reported that α-halomethyl ornithines capable of irreversible ODC inhibition, in combination with known cytotoxic agents has demonstrated some synergistic effects in the treatment of such disease states.

Quite surprisingly we have discovered that another combination has demonstrated superior end-use characteristics by the unexpected and synergistic effects in the treatment of rapidly proliferating tumor tissue marked with an abnormal elevation of polyamine levels. This new aspect in the treatment of rapidly proliferating cell tissue diseases is the use of Interferon in conjunctive thereapy with irreversible ODC inhibitors. This discovery is all the more surprising in view of the generally acknowledged disappointment of Interferon as an effective chemotherapuetic agent in diseases of this nature.

According to the concepts of this invention, the improvement in the treatment of rapidly proliferating tumor tissue disease states is generic in nature in that it relates to any ornithine decarboxylase inhibitor found to be useful in treating such disease states. However, in the present state of the art the particularly preferred ODC inhibitors with which Interferon can be conjunctively administered for the treatment of tumor tissue diseases are methyl acetylenic putrescine and compounds of the formulae

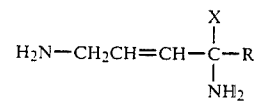

and

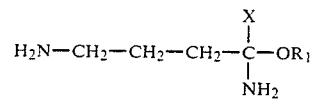

wherein X is —CHF$_2$ or —CH$_2$F,

R is H or COR$_1$,

R$_1$ is OH or C$_{1-6}$ lower alkoxy, and the pharmaceutically acceptable salts and individual optical isomers thereof. Particularly preferred compounds are α-difluoromethyl ornithine (α-DFMO), the methyl and ethyl esters of monofluoromethyl dehydroornithine, and the R,R-isomer of methyl acetylenic putrescine (i.e., (2R, 5R)-6-heptyne-2,5-diamine.

According to the concepts of this invention the term "Interferon" is used in its generic meaning. Although known for over twenty years, Interferon has not yet been sufficiently characterized as to be subject to a precise definition and thus some difficulty arises in the use of the term. However, it is a term that is attached to those glycoproteins which are made by all animal cells after viral attack, and which function as regulating functionaries of the immune system. Interferon has also been made biosynthetically by recombinant DNA techniques and thus the precise characterization and/or nomenclature of such substance has been further complicated. However, as used in the art and in the context of this application, the term Interferon is meant to include all those natural and biosynthetic interferons capable of immunomodulation and include Type I and Type II interferons as well as the recombinant DNA types. Type I interferons (also sometimes called leucocyte interferons) include those $\alpha$ and $\beta$ interferons generally prepared from leucocytes by viral infection. Type II interferons, sometimes called immunoactive interferon are those which are generally prepared from lymphocitic reactions with mitogenes. Although, as stated above, the recombinant interferons are included herein, the immune and leucocyte interferons are preferred. Also included within the concept of the present invention is the embodiment of the treatment of tumor tissue with ODC inhibitors and Interferon when the Interferon is generated by the use of Interferon inducers (e.g., tilorone and its related analogs known as interferon inducers) which, in situ, induce the release of Interferon.

A still further aspect of this invention is the use of Interferon in conjunctive therapy with known nonsteroidal anti-androgenic agents (e.g., Flutamide and the like), with or without the added effects of ODC inhibitors, in the treatment of androgen-dependent disease states such as benign prostatic hypertrophy, prostatic carcinoma, mammary carcinoma and other androgen-dependent tumor sites throughout the body.

The ability of compounds to irreversibly inhibit ornithine decarboxylase in vivo can be demonstrated as follows: An aqueous solution of the appropriate compound is given orally or parenterally to male mice or rats. The animals are sacrificed 1 to 48 hours after administration of the compound, and the ventral lobes of the prostate removed and homogenized. The activity of ornithine decarboxylase is measured as generally described by E. A. Pegg and H. G. Williams-Ashman, *Biochem. J.* 108, 533–539 (1968).

As used herein, the term "tumor tissue" means both benign and malignant tumors or neoplasms, and includes melanomas, lymphomas, leukemias, and sarcomas. Illustrative examples of tumor tissues are cutaneous tumors, such as malignant melanomas and mycosis fungoides; hematologic tumors such as leukemias, for example, acute lymphoblastic, acute myelocytic or chronic myelocytic leukemia; lymphomas, such as Hodgkin's disease or malignant lymphoma; gynecologic tumors, such as ovarian and uterine tumors; urologic tumors, such as those of the prostate, bladder or testis; soft tissue sarcomas, osseus or non-osseus sarcomas, breast tumors; tumors of the pituitary, thyroid and adrenal cortex; gastrointestinal tumors, such as those of the esophagus, stomach, intestine and colon; pancreatic and hepatic tumors; laryngeae papillomestasas and lung tumors.

The term "controlling the growth", as used herein, means slowing, interrupting, arresting, or stopping the growth and metastases of a rapidly proliferating tumor in a warm blooded animal; it being understood that treatment (controlling the growth of a tumor tissue) in a warm blooded animal with ODC inhibitors and Interferon, either with or without the added effects of a cytotoxic agent does not generally provide a "cure" for the tumor in the sense that necessarily the tumor tissue is destroyed or totally eliminated. Experimentally, however, some tumor tissues have been completely eliminated.

It is generally known, and for purposes of this invention, an ODC inhibitor can be administered to a patient in conjunction with other therapeutical methods or in combination with chemical agents known in the art to be useful for tumor therapy. For example, an ODC inhibitor can be administered in conjunction with surgical excision of the tumor or with radiation therapy, immunotherapy, or local heat therapy. Moreover, in a preferred manner, an ODC inhibitor can be administered to a patient in combination with a chemical cytotoxic agent known in the art to be useful for tumor therapy. When such combination therapy is employed for the treatment of a tumor, the cytotoxic agent may be administered at a dosage known in the art to be effective for treating the tumor. However, the ODC inhibitor may produce an additive or synergistic effect with a cytotoxic agent against a particular tumor. Thus, when such combination antitumor therapy is used, the dosage of the cytotoxic agent administered may be less than that administered when the cytotoxic agent is used alone. In combination with an ODC inhibitor, the cytotoxic agent may, therefore, be administered at a lower dosage level or at less frequent intervals as compared to the cytotoxic agent when used alone. Similarly, when Interferon is used with an ODC inhibitor, alone or in combination with a cytotoxic or other herein mentioned therapeutic agent, the dosage of the ODC inhibitor or other conjunctively utilized agent, may be less than when used without Interferon. Also, Interferon may not decrease the amount of ODC inhibitor or other agent but rather may function to increase the efficacy of these prior art agents.

When Interferon is used with an ODC inhibitor in conjuction with a cytotoxic agent most known cytotoxic agents may be employed. Illustrative examples of cytotoxic agents are: cyclophosphamide, methotrexate, prednisone, 6-mercaptopurine, procarbazine, daunorubicin, vincristine, vinblastine, chlorambucil, cytosine arabinoside, 6-thioguanine, thio TEPA, 5-fluorouracil, 5-fluoro-2-deoxyuridine, 5-azacytidine, nitrogen mustard, 1,3-bis(2-chloroethyl)-1-nitrosourea (BCNU), (1-(2-chloroethyl)-3-cyclohexyl-1-nitrosourea) (CCNU), busulfan, adriamycin, bleomycin, vindesine, cycloleucine or methylglyoxal bis(guanylhydrazone) (i.e., MGBG).

The effect of an ODC inhibitor for the control of the growth rate of rapidly proliferating tumor tissue can be assessed in standard animal tumor models. For example, the anti-tumor effect of $\alpha$-difluoromethylornithine (DFMO) has been demonstrated in the following animal tumor models: (a) L1210 leukemia in mice, (b) EMT6 tumor in Balb/C mice, (c) 7,12-dimethylbenzanthracene-induced (DMBA-induced) mammary tumor in rats, and (d) Morris 7288C or 5123 hepatoma in Buffalo rats. In addition, the anti-tumor effect of DFMO in combination with various cytotoxic agents has been demonstrated as follows: (a) in combination with vindesine or adriamycin in L1210 leukemia in mice, in Morris 7288C hepatoma in Buffalo rats, and in EMT6 tumor in mice, (b) in combination with cytosine arabinoside in L1210 leukemia in mice, (c) in combination with methotrexate in L1210 leukemia in mice, (d) in combination with cyclophosphamide in EMT6 tumor in mice and in DMBA-induced tumor in mice, (e) in combination with BCNU in mouse glioma 26 brain tumor, and (f) in combination with MGBG in L1210 leukemia in mice, in Morris 7288C hepatoma in Buffalo rats, in P388 lymphocytic leukemia in mice, and in S-180 sarcoma in mice.

The method of the present invention is particularly advantageous in that both the Interferon and the ODC inhibitors are essentially non-toxic.

When, in the treatment of a malignant neoplastic disease, an ODC inhibitor is administered in combination with a cytotoxic agent, the therapeutic effect of the cytotoxic agent may be potentiated. The remission produced by the cytotoxic agent may be enhanced and regrowth of the tumor tissue may be slowed or prevented. Use of such combination therapy therefor allows smaller doses or fewer individual doses of the cytotoxic agent to be employed. Thus, the detrimental and/or debilitating side effects of the cytotoxic agent are minimized while, at the same time, the anti-tumor effects are enhanced. The term "combination therapy" contemplates the administration of an ODC inhibitor immediately prior to the beginning of therapy with a cytotoxic agent, concomitantly with such therapy, or during the period of time immediately following cessation of such therapy. Preferably, the patient is treated with an ODC inhibitor for about 1 to 14 days, preferably 4 to 14 days, prior to the beginning of therapy with a cytotoxic agent, and thereafter, on a daily basis during the course of such therapy. Daily treatment with the ODC inhibitor can be continued for a period of, for example, 1 to 365 days after the last dose of the cytotoxic agent is administered.

When such combination therapy results in remission of the tumor, and all tumor cells are not destroyed, regrowth of the tumor may be prevented or slowed indefinitely by continued treatment with an ODC inhibitor. Thus, Interferon and an ODC inhibitor can be administered to stop or slow the growth of the tumor during the periods when therapy using a cytotoxic agent may be temporarily discontinued.

A preferred cytotoxic agent for combination therapy with an ODC inhibitor is methylglyoxal bis(guanylhydrazone), herein referred to as MGBG. The activity of MGBG as a cytotoxic agent in the treatment of neoplastic diseases is well documented. For example, W. A. Knight et al., Cancer Treat Rep., 43, 1933, (1979) have reported that a dose of MGBG administered intravenously once or twice a week to patients in the advanced stages of carcinoma of the bladder, esophagus, lung, pancreas, colon, kidney, breast and prostate, oat cell carcinoma, adenocarcinoma, lymphoma, hepatoma, melanoma, leukemia, or Ewing's sarcoma produced measurable regression of the tumor in many of the patients treated and complete disappearance of the disease in two of the 65 treated patients.

The amount of MGBG to be administered may be the same as the amount known in the art to be effective for tumor therapy. Effective and non-toxic dosages are determined by the physician in each case, taking into account the condition of the individual patient. For example, a dosage of 250–500 mg per meter$^2$ of body surface area may be infused once or twice weekly in 100 ml of aqueous 5% dextrose solution over a 30 minute period. Combination therapy with an ODC inhibitor and Interferon improves the response of the tumor tissue to the cytotoxic effect of MGBG and permits the use of a smaller individual dose of MGBG and a shorter course of treatment than would be required with the use of MGBG alone.

Suitable dosages of α-DFMO or other ODC inhibitors for use in combination therapy with MGBG or other cytotoxic agents can be any amount effective in inhibiting polyamine biosynthesis sufficiently to control the tumor growth rate or to achieve a heightened response to the cytotoxic agent administered in conjunction therewith.

The synergistic cytotoxic effect on tumor tissue of an ODC inhibitor in combination with MGBG can be demonstrated quantitatively in cultures of HeLa cells. A HeLa cell culture grown under standard laboratory conditions was treated with MGBG at a concentration of 7 μM alone and with the same dosage of MGBG after pretreatment with 2,5-diamino-2-difluoromethylpentanoic acid (2.5 mM) for 4 days. The cell culture treated with MGBG alone showed a 25% cell kill, wherreas the culture pretreated with a compound of the present invention showed a cell kill of 97%.

As pharmacologically useful agents, the ODC inhibitors can be administered in various manners to the patient being treated to achieve the desired effect. The compounds or parenterally (for example, intravenously, intraperitoneally, or subcutaneously), including injection of the active ingredient directly into the tumor. The amount of compound administered will vary over a wide range and can be any effective amount. Depending upon the patient to be treated, the severity of the condition being treated, the mode of administration, and the particular compound employed, the effective amount of compound administered will vary from about 1 mg/kg to 2000 mg/kg of body weight of the patient per day and preferably will be about 10 mg/kg to 500 mg/kg of body weight of patient per day. For example, a typical unit dosage form may be a tablet containing from 100 to 500 mg of a compound which may be administered to the patient being treated 1 to 10 time daily to achieve the desired effect.

As used herein the term patient is taken to mean warm blooded animals such as mammals, for example, dogs, rats, mice, cats, guinea pigs, horsses, bovine cows, sheep, and humans.

The solid unit dosage forms can be of the conventional type. Thus, the solid form can be a capsul which can be of the ordinary gelatin type containing a novel compound of this invention and a carrier, for example, lubricant and inert fillers, such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions ethanols and glycols such as propylene glycol or polyethylene glycol are preferred liquid carriers, particularly for injectable solutions.

The results of ODC inhibitors in the treatment of rapidly proliferating tumor tissue disease states when used in combination with Interferon (IFN) have demonstrated a striking tumor suppression and such results can be shown and ascertained by standard and well-known laboratory techniques as may be illustrated by the following.

EXAMPLE I

EFFECT OF COMBINATION OF DFMO AND INTERFERON ON THE GROWTH OF B16 MELANOMA IN MICE

| Treatment | Tumor Weight in grams (Mean ± S.D.) | No. animals without detectable tumor[a] | % Inhibition of tumor growth |
|---|---|---|---|
| Control | 6.75 ± 1.82 | 0/20 | |
| Interferon | 5.12 ± 1.94* | 0/20 | 24 |
| DFMO | 1.05 ± 0.49** | 0/20 | 84 |
| DFMO + Interferon | 0.24 ± 0.11** | 4/20 | 96 |

*P < 0.05;
**P < 0.001
[a] by visual inspection for pigmentation.

$1 \times 10^5$ B16 melanoma cells were injected subcutaneously in the interscapular region of C57/BL mice. The animals were divided into 4 groups of 10 animals each. The first group was on normal drinking water and served as control. The second group received mouse fibroblast interferon (Type 1) 1000 units/mouse, s.c., starting on the 2nd day and alternate days thereafter up to the 20th day (10 doses). The third group received DFMO as a 2% aqueous solution in the drinking water (an oral dose of approximately 3 gr/kg/day based on fluid intake) starting 24 hours after tumor inoculation until the end of the experiment. The last group of animals received a combination of both DFMO and interferon treatments as described above. At the end of 3 weeks, the animals were sacrificed, tumors were dissected and weighed. A portion of the tumor tissue was used for polyamine analysis. The results presented are the average of two experiments. Statistical analysis was done according to Newman-Keuls procedure (15).

EXAMPLE II

EFFECT OF COMBINATION OF DFMO AND TYPE I MOUSE INTERFERON ON THE GROWTH AND METASTASES OF LEWIS LUNG CARCINOMA IN MICE

TUMOR GROWTH

| Treatment | Tumor Weight (Mean ± S.E.) | No. Animals Without Detectable Tumors | % Inhibition of Tumor Growth |
|---|---|---|---|
| Control | 6.46 ± 0.58 | 0/14 | |
| DFMO | 4.62 ± 0.62 | 0/15 | 28 |
| IFN | 6.3 ± 1.12 | 0/12 | 8 |
| DFMO + IFN | 0.15 ± 0.29** | 8/12 | 92 |

Pulmonary Metastases

| Treatment | No. of Foci (Mean ± S.E.) | No. Animals Without Detectable Metastase | % Inhibition of Metastases |
|---|---|---|---|
| Control | 18.0 ± 4.18 | 1/14 | |
| DFMO | 1.7 ± 0.89** | 10/15 | 91 |
| IFN | 16.9 ± 5.93 | 1/12 | 6 |
| DFMO + IFN | 0 | 12/12 | 100 |

**P < 0.01

$2 \times 10^5$ viable 3 LL cells/animal were injected at the interscapular region, DFMO was administered as 2% solution in the drinking water. Mouse type 1 interferon, 1000 units/mouse S.C., was administered on alternate days starting on day 2 up to 20th day (10 doses). At the end of 3 weeks, the animals were sacrificed, tumor dissected and weighed. Pulmonary metastases was determined by the India ink method of Wexler (1966).

The effect of an ODC inhibitor and interferon on the polyamine concentrations can be illustrated by the following examples

EXAMPLE III

EFFECT OF DFMO AND INTERFERON TREATMENT ON THE INTRACELLULAR POLYAMINE CONCENTRATIONS OF B16 MELANOMA CELLS IN CULTURE

| Treatment | Polyamine Concentration (n.moles/$10^6$ cells) | | |
|---|---|---|---|
| | Putrescine | Spermidine | Spermine |
| Control | 1.91 | 6.64 | 1.91 |
| DFMO (2.5 mM) | N.D. | 0.22 | 1.39 |
| Interferon (100 units/ml) | 0.14 | 3.92 | 2.17 |
| DFMO + Interferon | N.D. | 0.24 | 1.74 |

The culture conditions are described as follows: B-16 melonoma cells were placed at a density of $1 \times 10^5$ cells/35 mm disk and treated with DFMO and Interferon (100 units/ml). At the end of 5 days of incubation at 37° C. in the presence of DFMO (2.5 mM) or interferon (100 units/ml) or a combination of these two agents, cells were collected by trypsinization, washed and counted. Two million cells were collected in duplicate for each sample, washed and extracted with 0.4 M perchloric acid. The supernatant was collected from the extract by centrifugation and the polyamines in the extracts were determined by dansylation and subsequent thin layer chromatography according to the procedure of Seiler (14). N. D.=not detectable (less than 20 pico moles detection limit).

EXAMPLE IV

EFFECT OF DFMO AND INTERFERON TREATMENT ON POLYAMINE CONCENTRATIONS IN B16 MELANOMA TUMOR IN MICE (n = 5)

| Treatment | Polyamine Levels (n. moles/gr. tumor; Mean ± S.D., n = 5) | | |
|---|---|---|---|
| | Putrescine | Spermidine | Spermine |
| Control | 24.5 ± 9.2 | 1139 ± 288 | 814 ± 149 |
| DFMO | N.D. | 47 ± 8 | 599 ± 125 |
| Interferon (IFN) | 35.1 ± 15.5 | 1129 ± 205 | 772 ± 125 |
| DFMO + IFN | N.D. | 71 ± 14 | 840 ± 104 |

The tumor tissues were collected from the animals described in Example 1. The tumor tissue was homogenized in 0.4 M perchloric acid and the supernatant obtained after centrifugation was used for polyamine determination by dansylation and subsequent thin layer chromatography according to the method of Seiler (14). N. D.=not detectable (less than 20 pico moles).

In utilizing interferon to enhance the efficacy of ODC inhibitors in the treatment of rapidly proliferating tumor tissue, warts, psoriasis and other conditions for which ODC inhibitors have been known to be useful and other disease states mentioned herein, the Interferon is generally utilized in amounts of about $10^3$–$10^8$ units of interferon daily, although it is expected that the preferred range will be about $10^5$ to $10^6$ units of interferon.

When using α-DFMO as the ODC inhibitor with which interferon is administered in combination via infusion, the daily infusion dose of α-DFMO can vary between 10 and 20 grams per day. The current formula of injectable is 100 mg/ml so the daily infused volume could vary from 100 ml to 200 ml. Analogous amounts of other ODC inhibitors can be determined by standard techniques, (e.g., comparing potencies, etc. with α-DFMO).

The ratio of α-DFMO and interferon can be altered to provide the daily dose of each in one product given by infusion once a day. Examplary formulations are as follows.

EXAMPLE V

| Sterile Powder Blend for Reconstitution | |
|---|---|
| α-DFMO | 2000 mg |
| Interferon | $10^5$ to $10^6$ units |

To be reconstituted with 20 ml. water for injection just prior to infusion.

EXAMPLE VI

| Sterile Lyophillized Powder for Reconstitution | |
|---|---|
| α-DFMO | 2000 mg. |
| Interferon | $10^5$ to $10^6$ units |

To be reconstituted with 20 ml. water for injection just prior to infusion.

EXAMPLE VII

| Preconstituted Sterile Solution for Infusion | |
|---|---|
| α-DFMO | 2000 mg. |
| Interferon | $10^5$ to $10^6$ units |

Water for injection q.s. 20 ml.

The α-DFMO being a strong buffer agent in the acid range, enchances the stability of the interferon.

Of course the ODC inhibitors and the interferon can be administered separately depending upon the judgement of the attending diagnostician.

Another application of the enhancement of treatment with the combination of an ODC inhibitor and interferon (with or without another chemotherapeutic agent) is the enhanced treatment of "secondary" viral infections in those subjects who have lost their natural immunity from other treatments.

It is to be noted that S-adenosylmethionine decarboxylase (SAM-DC) inhibitors are generally known to inhibit the synthesis of spermidine and spermine from putrescine and that MGBG is a preferred example.

Still another aspect of this invention relating to the treatment of rapidly proliferating tumor tissue disease states with ODC inhibitors (with or without cytotoxic agents) is the use of other immunomodulating agents (natural or synthetic) in conjunctive therapy with the ODC inhibitors. Immunomodulating agents such as bacillus calmette-gueran, *corynebacterium parvum*, tuftsin, pyran co-polymers, pyrimidinone type compounds, (e.g., 2-amino-5-bromo-6-phenyl-4(3H)pyrimidinone), propanediamine, levamisole, and the like would be useful in enhancing the effects derived with ODC inhibitors. For example, treatment of B16 melonoma (F1) tumor-bearing animals with a combination of DFMO (2% in drinking water) and tuftsin (25 μg/mouse, s.c. for 10 days) resulted in inhibition of putrescine and spermidine levels to 90% and 94% respectively in the tumor tissue. A combination treatment with these two agents resulted in 97% inhibition of tumor growth, while 80% and 24% inhibition respectively were observed with DFMO and tuftsin given alone. These data indicate the potential usefulness of the inhibitors of polyamine biosynthesis in combination with tuftsin and the other foregoing immunomodulating agents in cancer chemotherapy. When used, such immunomodulating agents may be administered in conjunctive therapy by intravenous administration at their presently known useful therapeutic dosages.

What is claimed is:

1. In the process of effecting polyamine depletion with ornithine decarboxylase inhibitors and with S-adenosylmethionine decarboxylase inhibitors useful in the treatment of rapidly proliferating tumor tissue disease states the improvement which comprises the use of an effective amount of interferon in conjunctive therapy therewith.

2. A process of claim 1 wherein the interferon is utilized with an ornithine decarboxylase inhibitor.

3. A process of claim 2 wherein the ornithine decarboxylase inhibitor is α-difluoromethyl ornithine or a pharmaceutically acceptable salt thereof.

4. A process of claim 2 wherein the ornithine decarboxylase inhibitor is the methyl ester of monofluoromethyl dehydroornithine or a pharmaceutically acceptable salts thereof.

5. A process of claim 2 wherein the ornithine decarboxylase inhibitor is the R,R-isomer of methyl acetylenic putrescine or a pharmaceutically acceptable salt thereof.

6. A process of claim 1 wherein the interferon is utilized with an S-adenosylmethionine decarboxylase inhibitor.

7. A processor of claim 6 wherein the S-adenosylmethionine decarboxylase inhibitor is methylglyoxal bis(guanylhydrazone).

8. A process of claim 1 wherein the interferon is utilized with the conjunctive effects of α-difluoromethyl ornithine and methylglyoxal bis(guanylhydrazone).

9. A process of claim 1 wherein the polyamine depletion effect is utilized in controlling the growth rate of rapidly proliferating tumor tissue in a patient in need thereof.

10. A process of claim 9 wherein the ornithine decarboxylase inhibitor is α-difluoromethyl ornithine or pharmaceutically acceptable salt thereof.

11. A process of claim 9 wherein the ornithine decarboxylase inhibitor is methyl ester of monofluoromethyl dehydroornithine or a pharmaceutically acceptable salt thereof.

12. A process of claim 9 wherein the ornithine decarboxylase inhibitor is the R,R-isomer of methyl acetylenic putrescine or a pharmaceutically acceptable salt thereof.

13. A process according to claims 2 or 3 wherein the disease state is Malignant Melonoma.

14. A process according to claims 2 or 3 wherein the disease state is Chronic Myelogenous Leukemia.

15. A process according to claims 2 or 3 wherein the disease state is Renal Cell Carcinoma.

* * * * *